(12) United States Patent
Sridhar et al.

(10) Patent No.: US 11,542,268 B2
(45) Date of Patent: Jan. 3, 2023

(54) CATIONICALLY CURABLE COMPOSITIONS WITH LATENT REDUCING AGENT DEMONSTRATING LOW CURE TEMPERATURE

(71) Applicant: Henkel AG & Co. KGaA, Duesseldorf (DE)

(72) Inventors: Laxmisha M. Sridhar, Monmouth Junction, NJ (US); Timothy M. Champagne, Anaheim, CA (US)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 17/130,213

(22) Filed: Dec. 22, 2020

(65) Prior Publication Data
US 2021/0107915 A1 Apr. 15, 2021

Related U.S. Application Data

(63) Continuation of application No. PCT/US2019/039370, filed on Jun. 27, 2019.

(60) Provisional application No. 62/691,028, filed on Jun. 28, 2018.

(51) Int. Cl.
| | | |
|---|---|---|
| *C08G 59/68* | (2006.01) | |
| *C08L 63/04* | (2006.01) | |
| *B01J 31/02* | (2006.01) | |
| *B01J 31/22* | (2006.01) | |
| *C07D 491/18* | (2006.01) | |

(52) U.S. Cl.
CPC ........ *C07D 491/18* (2013.01); *B01J 31/0231* (2013.01); *B01J 31/2295* (2013.01); *C08G 59/687* (2013.01); *C08L 63/04* (2013.01); *B01J 2523/842* (2013.01)

(58) Field of Classification Search
CPC . C07D 491/18; B01J 31/0231; B01J 31/2295; B01J 2523/842; C08G 59/687; C08L 63/04
USPC ........................................................ 528/412
See application file for complete search history.

(56) References Cited

U.S. PATENT DOCUMENTS

| | | |
|---|---|---|
| 4,275,190 A | 6/1981 | Dudgeon |
| 4,482,679 A | 11/1984 | Irving |
| 6,355,750 B1 | 3/2002 | Herr |
| 2003/0199638 A1 | 10/2003 | Liu et al. |
| 2013/0164230 A1* | 6/2013 | Scheurich ............... A61P 17/00 424/59 |
| 2016/0002510 A1 | 1/2016 | Champagne et al. |
| 2017/0183450 A1 | 6/2017 | Leon et al. |

FOREIGN PATENT DOCUMENTS

| | | |
|---|---|---|
| DE | 4325846 | 1/1995 |
| EP | 2440627 B1 | 3/2015 |

OTHER PUBLICATIONS

Crivello, J.V. et al. "Redox-Initiated Cationic Polymerization: The Diaryliodonium Salt/Benzoin Redox Couple" Journal of Polymer Science: Polymer Chemistry Edition, John Wiley & Sons, Inc., vol. 21, 1983, pp. 1097-1110.

Cao Hua et al.: "An Efficient and General Iron-Catalyzed One-PotSynthesis of Furans via [alpha]-Hydroxy Ketones and Activated Alkynes", European Journal of Organic Chemistry, vol. 2012, No. 12 (2012).

* cited by examiner

*Primary Examiner* — David T Karst
(74) *Attorney, Agent, or Firm* — Steven C. Bauman

(57) ABSTRACT

Cationically curable compositions with latent reducing agents that demonstrate low cure temperature and improved work life are provided.

13 Claims, No Drawings

CATIONICALLY CURABLE COMPOSITIONS WITH LATENT REDUCING AGENT DEMONSTRATING LOW CURE TEMPERATURE

BACKGROUND

Field

Cationically curable compositions with latent reducing agents that demonstrate low cure temperature and improved work life are provided.

Brief Description of Related Technology

In many manufacturing and packaging processes, good processing speed leads to higher throughput and lower assembly costs. When the use of an adhesive, coating, or encapsulant is part of the manufacturing process, processing speed can be increased if the adhesive, coating, or encapsulant can be cured quickly, desirably at a relatively low curing temperature. In the electronics packaging industry, for example, fast (snap) cure adhesives and encapsulants are desired for various applications. A common mode of electronic packaging involves affixing semiconductor devices onto substrates by an adhesive or encapsulant. The more prominent uses are the bonding of integrated circuit chips to metal lead frames or organic substrates, and the bonding of circuit packages or assemblies to printed wire boards, including, for example, die attach for array package, die attach for RFID package, and component attach for ink jet cartridge assembly. For ink jet cartridge, low temperature cure assembly can minimize jetting trajectory distortion and improve printing quality. For temperature-sensitive components or substrates, such as, the paper-based antenna in RFID application and camera sensor in organic substrates, low temperature interconnect is very desirable. Thus, many commercial opportunities exist for compositions that cure at low temperatures, preferably less than 100° C.

The redox cationic polymerization of epoxy resins using iodonium salts/copper salts is a well known process. U.S. Pat. No. 4,275,190 describes redox cationic polymerization of epoxy resins using a combination of iodonium and copper salts. Both Cu(I) and Cu(II) exhibit a catalytic effect in this cationic polymerization. When Cu(II) is used, higher temperatures are needed to achieve cure than when Cu(I) is used. To make the use of Cu(II) more attractive for lower temperature cure conditions, several activated α-hydroxyketone compounds such as those present in benzoin and furoin have been used as reducing agents for Cu(II). U.S. Pat. No. 4,482,679 describes a curable composition of an iodonium salt and Cu(II) salts in combination with reducing agents for Cu(II) in a 3-component curing system. J. Crivello et al., *J. Polym. Sci., Polym. Chem.*, 21, 1097 (1983) describe a 3-component curing system for epoxy resins of iodonium salts, copper (II) salts and co-reducing agents, namely, activated α-hydroxyketone compounds such as benzoin and furoin.

However, the latency of these cure systems is not sufficient to achieve a good working life for the composition before premature gelation sets in. For many low temperature cure applications, good viscosity stability over a span of a few hours at room temperature is desired. To date, that has been a long standing yet unmet desire. Until now.

SUMMARY

Provided herein is a reaction product of furoin or a furoin derivative and certain other compounds that create a latent reducing agent so that both low temperature cure and good latency are achieved in cationically curable compositions.

More specifically, provided herein is a reaction product of furoin or a furoin derivative and (a) a compound having one or more maleimide, nadimide or itaconimide functional groups and/or (b) a compound having one or more maleate or fumarate functional groups.

This reaction product may be used in a curable composition comprising an epoxy-containing or oxetane-containing component, a cationic onium catalyst and a transition metal salt.

DETAILED DESCRIPTION

As noted above, provided herein in one aspect is a reaction product of furoin or a furoin derivative and (a) a compound having one or more maleimide, nadimide or itaconimide functional groups and/or (b) a compound having one or more maleate or fumarate functional groups.

The compound having one or more maleimide, nadimide, or itaconimide functional groups is embraced by

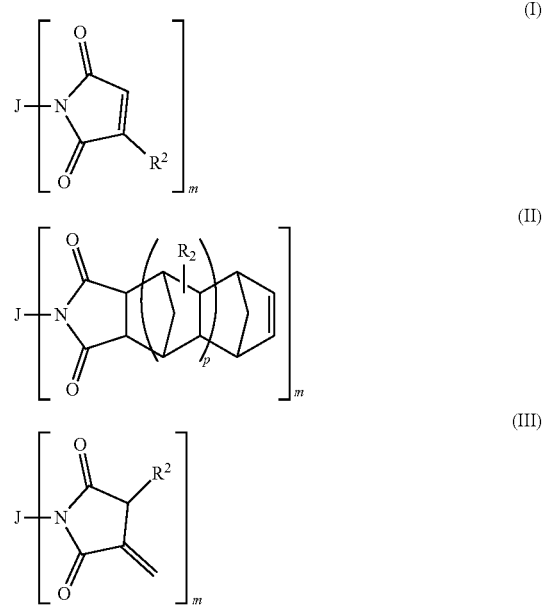

respectively, where:
m=1-15,
p=0-15,
each $R^2$ is independently selected from hydrogen or lower alkyl having from 1 to about 4 carbon atoms, and
J comprises a monovalent or a polyvalent moiety comprising organic or organosiloxane radicals, and combinations thereof.

More specifically, The "J" appendage of the maleimide-, nadimide- or itaconimide-containing compound may be viewed as a monovalent or polyvalent radical selected from hydrocarbyl, substituted hydrocarbyl, heteroatom-containing hydrocarbyl, substituted heteroatom-containing hydrocarbyl, hydrocarbylene, substituted hydrocarbylene, heteroatom-containing hydrocarbylene, substituted heteroatom-containing hydrocarbylene, polysiloxane, polysiloxane-polyurethane block copolymer, and combinations thereof, optionally containing one or more linkers selected from a covalent bond, —O—, —S—, —NR—, —O—C (O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, —NR—P(O)R$_2$—, where each R is independently hydrogen, alkyl or substituted alkyl, and combinations of any two or more thereof.

When one or more of the above described monovalent or polyvalent groups contain one or more of the above described linkers to form the "J" appendage of a maleimide, nadimide or itaconimide group, as readily recognized by those of skill in the art, a wide variety of linkers can be produced, such as, for example, oxyalkyl, thioalkyl, aminoalkyl, carboxylalkyl, oxyalkenyl, thioalkenyl, aminoalkenyl, carboxyalkenyl, oxyalkynyl, thioalkynyl, aminoalkynyl, carboxyalkynyl, oxycycloalkyl, thiocycloalkyl, aminocycloalkyl, carboxycycloalkyl, oxycloalkenyl, thiocycloalkenyl, aminocycloalkenyl, carboxycycloalkenyl, heterocyclic, oxyheterocyclic, thioheterocyclic, aminoheterocyclic, carboxyheterocyclic, oxyaryl, thioaryl, aminoaryl, carboxyaryl, heteroaryl, oxyheteroaryl, thioheteroaryl, aminoheteroaryl, carboxyheteroaryl, oxyalkylaryl, thioalkylaryl, aminoalkylaryl, carboxyalkylaryl, oxyarylalkyl, thioarylalkyl, aminoarylalkyl, carboxyarylalkyl, oxyarylalkenyl, thioarylalkenyl, aminoarylalkenyl, carboxyarylalkenyl, oxyalkenylaryl, thioalkenylaryl, aminoalkenylaryl, carboxyalkenylaryl, oxyarylalkynyl, thioarylalkynyl, aminoarylalkynyl, carboxyarylalkynyl, oxyalkynylaryl, thioalkynylaryl, aminoalkynylaryl or carboxyalkynylaryl, oxyalkylene, thioalkylene, aminoalkylene, carboxyalkylene, oxyalkenylene, thioalkenylene, aminoalkenylene, carboxyalkenylene, oxyalkynylene, thioalkynylene, aminoalkynylene, carboxyalkynylene, oxycycloalkylene, thiocycloalkylene, aminocycloalkylene, carboxycycloalkylene, oxycycloalkenylene, thiocycloalkenylene, aminocycloalkenylene, carboxycycloalkenylene, oxyarylene, thioarylene, aminoarylene, carboxyarylene, oxyalkylarylene, thioalkylarylene, aminoalkylarylene, carboxyalkylarylene, oxyarylalkylene, thioarylalkylene, aminoarylalkylene, carboxyarylalkylene, oxyarylalkenylene, thioarylalkenylene, aminoarylalkenylene, carboxyarylalkenylene, oxyalkenylarylene, thioalkenylarylene, aminoalkenylarylene, carboxyalkenylarylene, oxyarylalkynylene, thioarylalkynylene, aminoarylalkynylene, carboxy arylalkynylene, oxyalkynylarylene, thioalkynylarylene, aminoalkynylarylene, carboxyalkynylarylene, heteroarylene, oxyheteroarylene, thioheteroarylene, aminoheteroarylene, carboxyheteroarylene, heteroatom-containing di- or polyvalent cyclic moiety, oxyheteroatom-containing di- or polyvalent cyclic moiety, thioheteroatom-containing di- or polyvalent cyclic moiety, aminoheteroatom-containing di- or polyvalent cyclic moiety, carboxyheteroatom-containing di- or polyvalent cyclic moiety, disulfide, sulfonamide, and the like.

Compounds having one or more maleimide, nadimide, and/or itaconimide functional groups include those embraced by structures I, II, or III, respectively, where m=1-6, p=0-6, and J is selected from:

a saturated straight chain alkyl or branched chain alkyl, optionally containing optionally substituted aryl moieties as substituents on the alkyl chain or as part of the backbone of the alkyl chain, and where the alkyl chains have up to about 20 carbon atoms;

a siloxane having the structure: —(C(R$^3$)$_2$)$_d$—[Si(R$^4$)$_2$—O]$_f$—Si(R$^4$)$_2$—(C(R$^3$)$_2$)$_e$—, —(C(R$^3$)$_2$)$_d$—C(R$^3$)—C(O)O—(C(R$^3$)$_2$)$_d$—[Si(R$^4$)$_2$—O]$_f$—Si(R$^4$)$_2$—(C(R$^3$)$_2$)$_e$—O(O)C—(C(R$^3$)$_2$)$_e$—, or —(C(R$^3$)$_2$)$_d$—C(R$^3$)—O(O)C—(C(R$^4$)$_2$)$_d$—[Si(R$^4$)$_2$—O]$_f$—Si(R$^4$)$_2$—(C(R$^3$)$_2$)$_e$—C(O)O—(C(R$^3$)$_2$)$_e$—, where:

each R$^3$ is independently hydrogen, alkyl or substituted alkyl, each R$^4$ is independently hydrogen, lower alkyl (i.e., 1 to about 4 carbon atoms) or aryl, d=1-10, e=1-10, and f=1-50;

a polyalkylene oxide having the structure:

$$[(CR_2)_r—O-]_f—(CR_2)_s—$$

where:

each R here is independently hydrogen, lower alkyl or substituted alkyl, r=1-10, s=1-10, and f is as defined above;

aromatic groups having the structure:

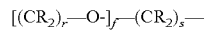

where:

each Ar is a monosubstituted, disubstituted or trisubstituted aromatic or heteroaromatic ring having in the range of 3 up to 10 carbon atoms, and Z is:

saturated straight chain alkylene or branched chain alkylene, optionally containing saturated cyclic moieties as substituents on the alkylene chain or as part of the backbone of the alkylene chain, or polyalkylene oxides having the structure:

$$—[(CR_2)_r—O-]_q—(CR_2)_s—$$

where:

each R is independently selected from hydrogen or lower alkyl (i.e., 1 to about 4 carbon atoms), r and s are each defined as above, and q falls in the range of 1 up to 50;

di- or tri-substituted aromatic moieties having the structure:

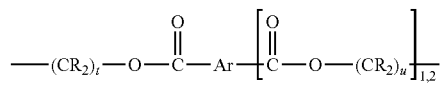

where:

each R is independently selected from hydrogen or lower alkyl, t falls in the range of 2 up to 10, u falls in the range of 2 up to 10, and Ar is as defined above;

aromatic groups having the structure:

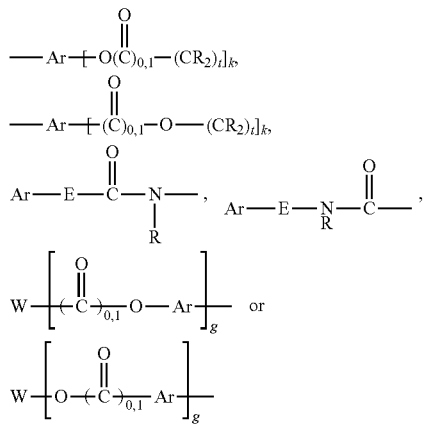

where:
each R is independently selected from hydrogen or lower alkyl,
t=2-10,
k=1, 2 or 3,
g=1 up to about 50,
each Ar is as defined above,
E is —O— or —NR$^5$—, where R$^5$ is hydrogen or lower alkyl, and
W is straight or branched chain alkyl, alkylene, oxyalkylene, alkenyl, alkenylene, oxyalkenylene, ester, or polyester, a siloxane having the structure —(C(R$^3$)$_2$)$_d$—[Si(R$^4$)$_2$—O]$_f$—Si(R$^4$)$_2$—(C(R$^3$)$_2$)$_e$—, —(C(R$^3$)$_2$)$_d$—C(R$^3$)—C(O)O—(C(R$^3$)$_2$)$_d$—[Si(R$^4$)$_2$—O]$_f$—Si(R$^4$)$_2$—(C(R$^3$)$_2$)$_e$—O(O)C—(C(R$^3$)$_2$)$_e$—, or —(C(R$^3$)$_2$)$_d$—C(R$^3$)—O(O)C—(C(R$^3$)$_2$)$_d$—[Si(R$^4$)$_2$—O]$_f$—Si(R$^4$)$_2$—(C(R$^3$)$_2$)$_e$—C(O)O—(C(R$^3$)$_2$)$_e$—, where:
each R$^3$ is independently hydrogen, alkyl or substituted alkyl,
each R$^4$ is independently hydrogen, lower alkyl or aryl,
d=1-10,
e=1-10, and
f=1-50; or a polyalkylene oxide having the structure:

—[(CR$_2$)$_r$—O-]$_f$—(CR$_2$)$_s$— where:
each R is independently hydrogen, alkyl or substituted alkyl,
r=1-10,
s=1-10, and
f is as defined above;
optionally containing substituents selected from hydroxy, alkoxy, carboxy, nitrile, cycloalkyl or cycloalkenyl;
a urethane group having the structure:

R$^7$—U—C(O)—NR$^6$—R$^8$—NR$^6$—C(O)—(O—R$^8$—O—C(O)—NR$^6$—R$^8$—NR$^6$—C(O))$_v$—U—R$^8$— where:
each R$^6$ is independently hydrogen or lower alkyl,
each R$^7$ is independently an alkyl, aryl, or arylalkyl group having 1 to 18 carbon atoms,
each R$^8$ is an alkyl or alkyloxy chain having up to about 100 atoms in the chain, optionally substituted with Ar,
U is —O—, —S—, —N(R)—, or —P(L)$_{1,2}$-, where R as defined above, and where each L is independently =O, =S, —OR or —R; and
v=0-50;
polycyclic alkenyl; or combinations thereof.

In a particularly desirable aspect of the invention, the maleimide, itaconimide and/or nadimide functional group of the maleimide, itaconimide and/or nadimide compound, respectively, is attached to J, a monovalent radical, or the maleimide, itaconimide and/or nadimide functional groups of the maleimide, itaconimide and/or nadimide compound are separated by J, a polyvalent radical, each of the monovalent radical or the polyvalent radical having sufficient length and branching to render the maleimide, itaconimide and/or nadimide compound a liquid.

In a more specific aspect thereof, J comprises a branched chain alkyl, alkylene or alkylene oxide species having sufficient length and branching to render the maleimide, itaconimide or nadimide compound a liquid, each R$^2$ is independently selected from hydrogen or methyl and m is 1, 2 or 3.

Certain maleimide-containing compounds useful in the practice of the present invention include, for example, maleimides having the following structures:

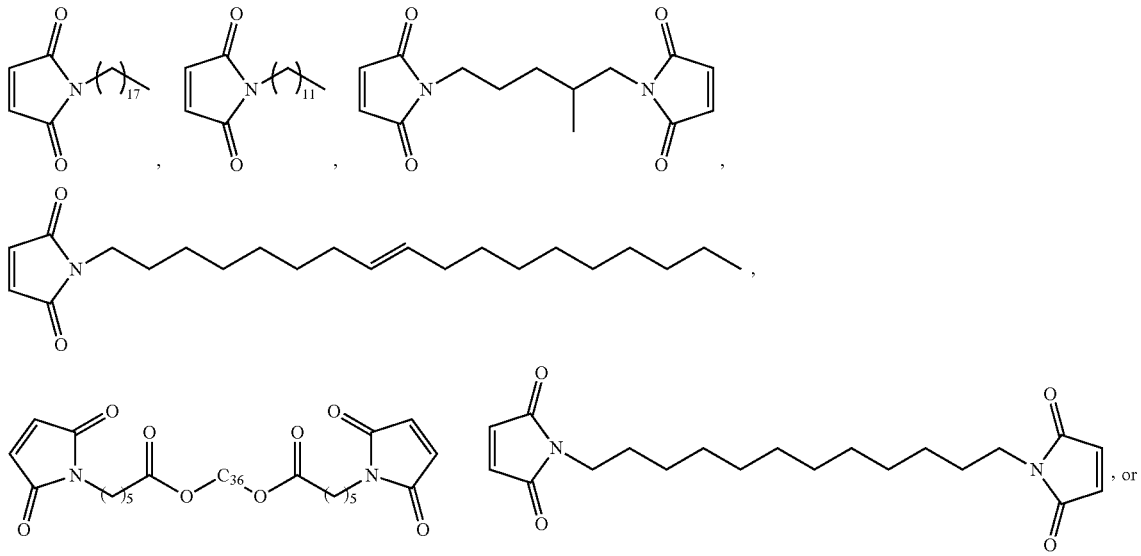

SRM-1

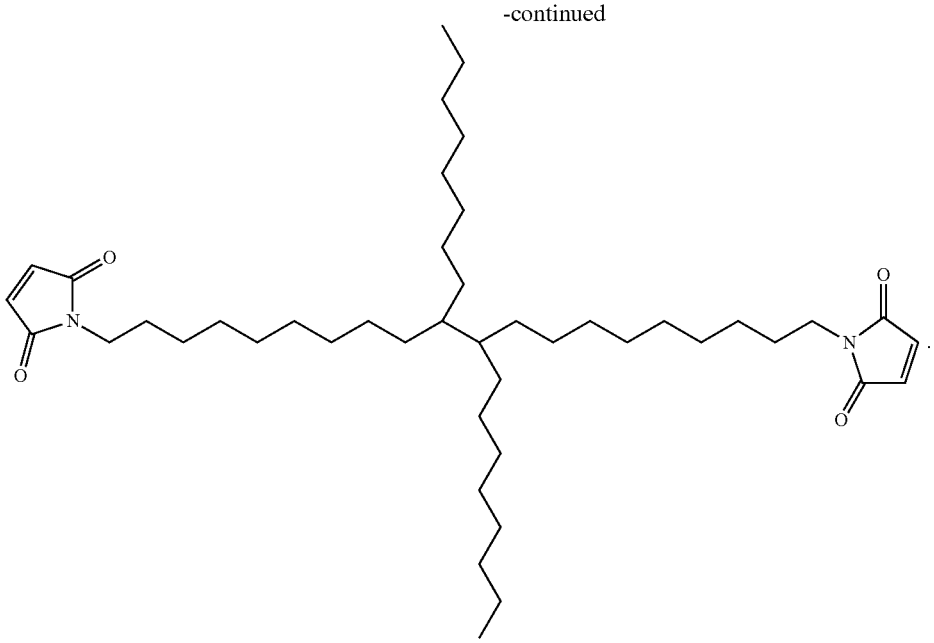

Additional maleimide-containing compounds of formula I include stearyl maleimide, oleyl maleimide, behenyl maleimide, 1,20-bismaleimido-10,11-dioctyl-eicosane, and the like, as well as combinations thereof.

Particularly desirable maleimide compounds embraced by formula I include bismaleimides prepared by reaction of maleic anhydride with dimer amines. An exemplary bismaleimide which can be prepared from such dimer amines is 1,20-bismaleimido-10,11-dioctyl-eicosane, which would likely exist in admixture with other isomeric species produced in the ene reactions employed to produce dimer acids. Other bismaleimides contemplated for use in the practice of the present invention include bismaleimides prepared from aminopropyl-terminated polydimethyl siloxanes (such as "PS510" sold by Hüls America, Piscataway, N.J.), polyoxypropylene amines (such as "D-230", "D-400", "D-2000" and "T-403", sold by Texaco Chemical Company, Houston, Tex.), polytetramethyleneoxide-di-p-aminobenzoates (such as the family of such products sold by Air Products, Allentown, Pa., under the trade name "VERSALINK", e.g., "VERSALINK" P-650), and the like. Preferred maleimide resins include stearyl maleimide, oleyl maleimide, behenyl maleimide, 1,20-bismaleimido-10,11-dioctyl-eicosane, and SRM-1, which is a Fischer esterification product of 6-maleimidocaproic acid and dimer diol (Pripol 2033, commercially available from Croda), as well as mixtures of any two or more thereof.

Bismaleimides can be prepared employing techniques well known to those of skill in the art, and as such will not be repeated here.

In another embodiment, instead of or in addition to the compound having one or more maleimide, nadimide, or itaconimide functional groups, may be a compound having one or more maleate (formula IV) and fumarate (formula V) functional groups embraced by

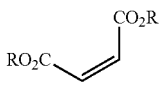

IV

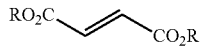

V respectively, where each R is independently selected from alkyl groups having from 1 to about 20 carbon atoms, cycloalkyl groups having from 3 to about 10 carbon atoms, aryl groups and alkaryl groups having from 7 to about 10 carbon atoms.

More specifically, the compound having one or more maleate and fumarate functional groups include alkyl esters of maleates and fumarates such as dimethyl, diethyl, dibutyl, dioctyl maleate and fumarate esters.

The furoin or furoin derivative should be used in at least 1:1 molar ratio to the compound having one or more maleimide, nadimide, or itaconimide functional groups and/or the compound having one or more maleate and fumarate functional groups in order to make the inventive reaction product, practical examples of which are described later. Since any residual free furoin can negatively affect work life, a slight excess of maleimide is used as compared to the furoin.

While furoin is commercially available not many furoin derivatives are commercially available. Representative furoin derivatives that can be used in the invention to form a Diels-Alder adduct may be embraced by the formula below

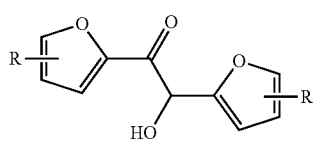

where R here may be substituted at any one or more of the free position(s) on either or both of the furan ring(s) and R may be selected from alkyl, aryl, halo, hydroxyalkyl, alkoxy, alkoxycarbonyl, thioether, or acetoxyalkyl, where the alkyl groups have from one to four carbon atoms. These derivatives may be made by benzoin type condensation reaction in one-step using furfural derivatives as a starting material as shown below by one skilled in the art.

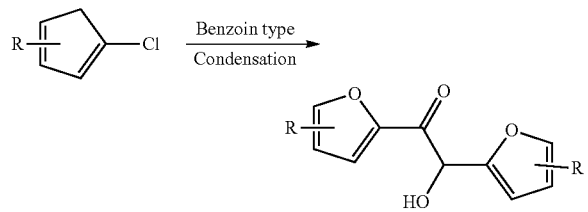

Many substituted furfural derivatives are commercially available and can be used to make furoin derivatives as shown above. Representative furfural derivatives from which the furoin derivatives may be made include, 5-methylfurfural, 5-hydroxymethylfurfural, 5-phenylfuraldehyde, 5-(4-bromophenyl)furfural, 5-bromo-2-furaldehyde, 5-cyano-2-furaldehyde, 5-acetoxymethyl-2-furaldehyde.

The inventive curable composition includes not only the so-described inventive reaction product, but also an epoxy-containing or oxetane-containing component, a cationic catalyst and a transition metal salt.

The inventive reaction product (sometimes called, Adduct or Diels-Alder adduct) should be used in an amount of about 0.1 to about 20 percent by weight in the cationically curable composition.

The epoxy-containing component should be selected from cycloalphatic epoxy resins; $C_4$-$C_{28}$ alkyl glycidyl ethers; $C_1$-$C_{28}$ alkyl-glycidyl esters; $C_2$-$C_{28}$ alkenyl-glycidyl esters; $C_1$-$C_{28}$ alkyl-, mono- and poly-phenol glycidyl ethers; polyglycidyl ethers of pyrocatechol, resorcinol, hydroquinone, 4,4'-dihydroxydiphenyl methane (or bisphenol F), 4,4'-dihydroxy-3,3'-dimethyldiphenyl methane, 4,4'-dihydroxydiphenyl dimethyl methane (or bisphenol A), 4,4'-dihydroxydiphenyl methyl methane, 4,4'-dihydroxydiphenyl cyclohexane, 4,4'-dihydroxy-3,3'-dimethyldiphenyl propane, 4,4'-dihydroxydiphenyl sulfone, and tris(4-hydroxyphyenyl)methane; polyglycidyl ethers of the chlorination and bromination products of the above-mentioned diphenols; polyglycidyl ethers of novolacs; polyglycidyl ethers of diphenols obtained by esterifying ethers of diphenols obtained by esterifying salts of an aromatic hydrocarboxylic acid with a dihaloalkane or dihalogen dialkyl ether; polyglycidyl ethers of polyphenols obtained by condensing phenols and long-chain halogen paraffins containing at least two halogen atoms; phenol novolac epoxy resins; cresol novolac epoxy resins; and combinations thereof.

The oxetane-containing component should be selected from mono- or multi-functional aliphatic or aromatic oxetane ester resins embraced by the following general structure, in which R is a methyl or ethyl group and n is 1 to 6:

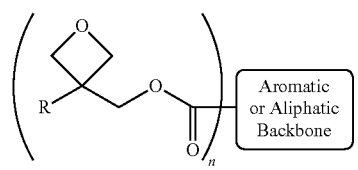

More specifically, aromatic oxetane esters may be embraced by the following general structure, in which R is a methyl or ethyl group and Ar is an aromatic group:

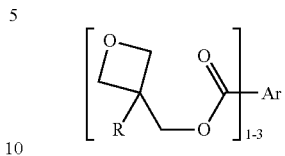

Ar may be any aromatic group with its carbon to carbon double bonds in conjugation with the carbon to oxygen double bond of the ester group. Ar may be substituted by alkyl, ether or ester functional groups.

In some embodiments, Ar is a single aryl group, two fused aryl groups, or two or more aryl groups connected by a direct bond, a lower alkylene (such as a one to four carbon atom alkylene linkage), or a heteroatom, such as oxygen or sulfur.

In other embodiments, Ar is two or more aryl groups connected by a linking group selected from

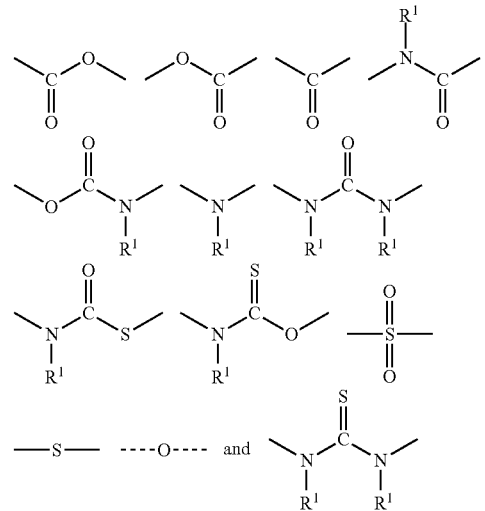

in which $R^1$ is a lower alkyl group (where lower is as exemplified above).

In one embodiment, oxetane ester functionalities are attached to an aliphatic backbone selected from linear, branched, or cycloalkylene groups, which optionally contain heteroatoms (such as O, S, halogens, Si, and N) or aromatic interruptions or substitutions.

In another embodiment, oxetane ester functionalities are attached to an aromatic backbone with its carbon to carbon double bonds in conjugation with the carbon to oxygen double bond of the ester group.

Or, aromatic oxetane esters may be embraced by the following general structure, in which R is a methyl or ethyl group, K is C(=O)O, G may or may not be present, but when present is $(CH_2)_mO$, where m is 1-4, and X is O, S, $SO_2$, C(=O), phenaldehyde, $CH_2$ or $C_3H_7$, and n is 1-3:

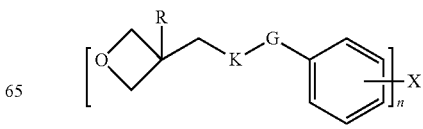

Or, phenoxy oxetane esters may be embraced by the following general structure, in which R is a methyl or ethyl group, X is an alkyl of from 1 to 5 carbon atoms or an alkylene of from 3 to 10 carbon atoms, either of which being substituted or interrupted by a heteroatom, such as O, N or S, or a biphenyl or a bisphenol A, E, F or S structure, and n is 1-3:

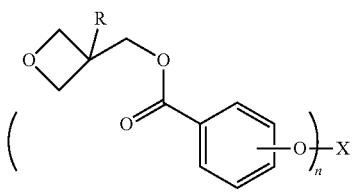

Still more specifically, phenoxy oxetane ethers may be embraced by the following general structure, in which R is a methyl or ethyl group, X is an alkyl of from 1 to 5 carbon atoms or an alkylene of from 3 to 10 carbon atoms, either of which being substituted or interrupted by a heteroatom, such as O, N or S, or interrupted by a ketone, an aryl, or a phenaldehyde, and n is 1-3:

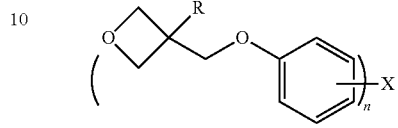

Representative oxetane-containing compounds suitable for use herein include:

OX-1

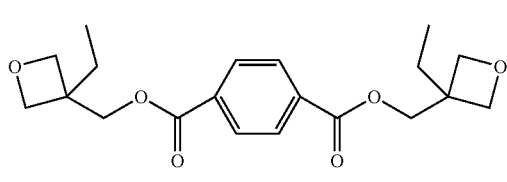

OX-2

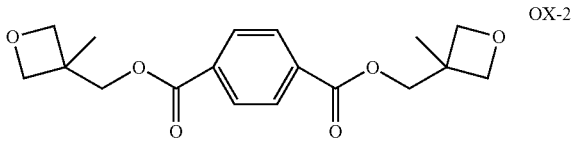

OX-3

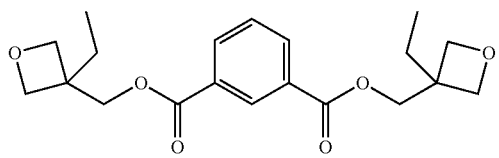

OX-4

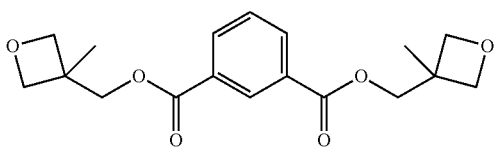

OX-5

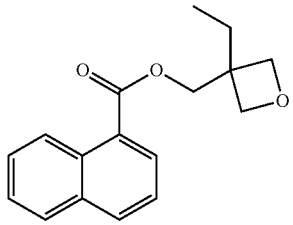

OX-6

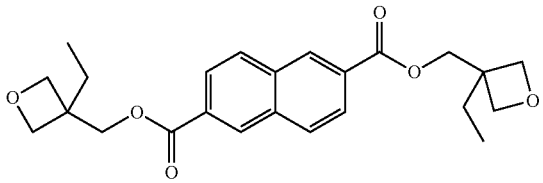

OX-7

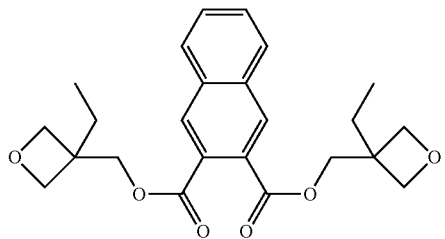

OX-8

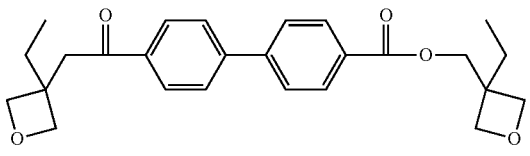

OX-9

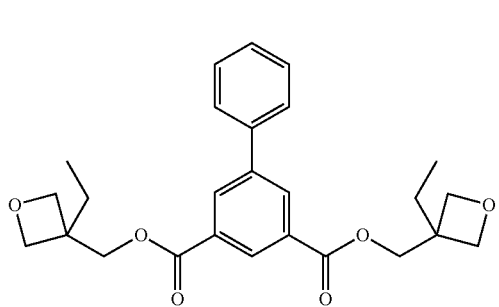

OX-10

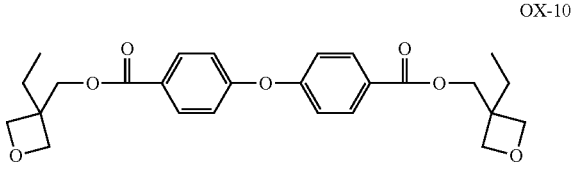

-continued
OX-11
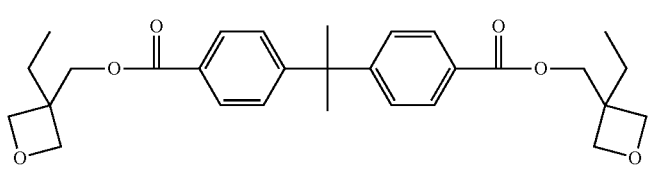
OX-12
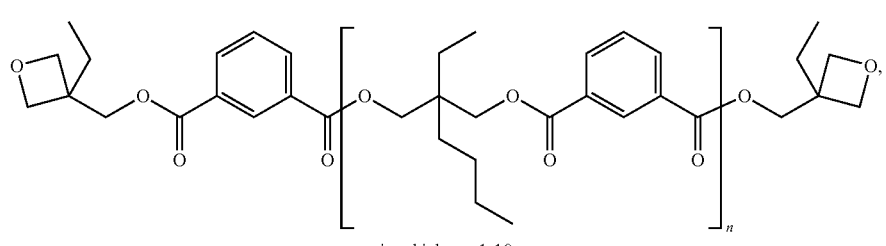
in which n = 1-10
OX-13
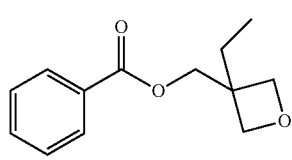
OX-14
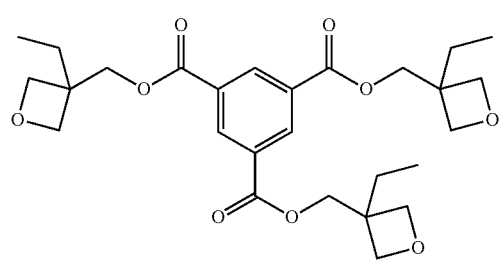
OX-15
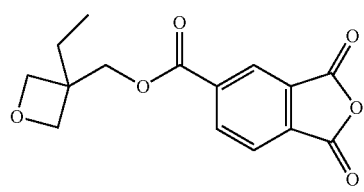
OX-16
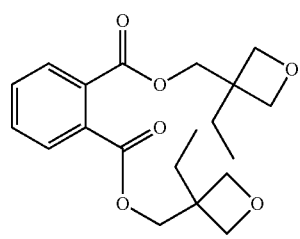
OX-17
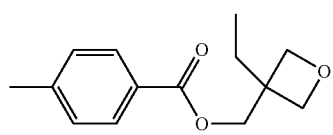
OX-18
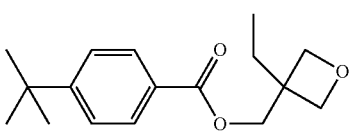
OX-19
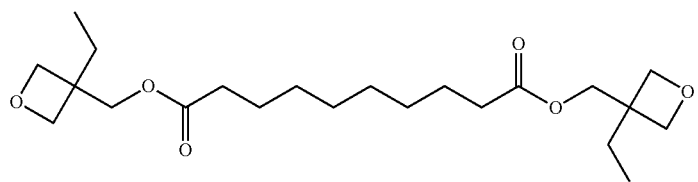

-continued

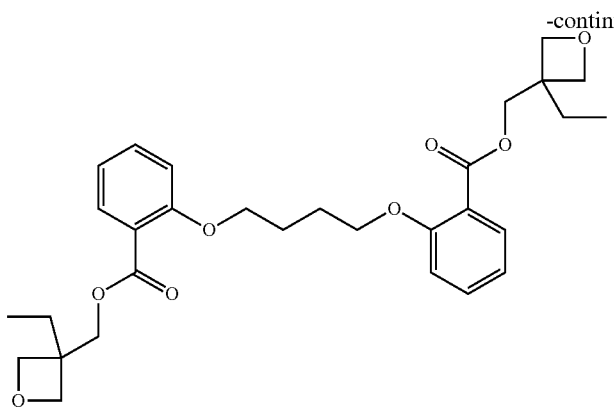
OX-20

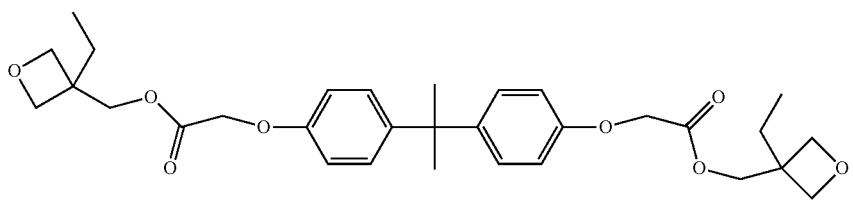
OX-21

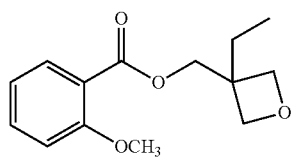
OX-22

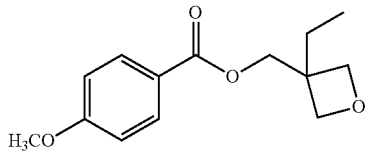
OX-23

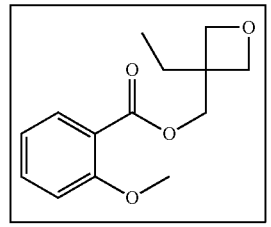
OX-24

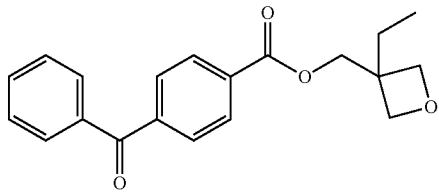
OX-25

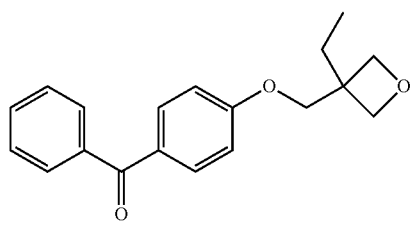
OX-26

Either a methyl group or an ethyl group may be attached to the carbon in the 3 position on the oxetane ring. Where one group is shown, the other group may be substituted.

It may be desirable to introduce the oxetane by way of polymeric or elastomeric resin. In such a situation, the oxetane or oxetane ester functionalities are present at terminus of, and/or as pendant groups on, a polymeric backbone. Representative polymer backbones include, but are not limited to, poly(meth)acrylates, polyolefins, polystyrene, polyesters, polyimides, polycarbonates, polysulfones, polysiloxanes, polyphosphazenes, and novolac resins.

In one embodiment, the oxetane-containing compounds are selected from OX-1, OX-2, OX-3, and OX-4.

Certain other oxetane-containing compounds are also provided. For instance

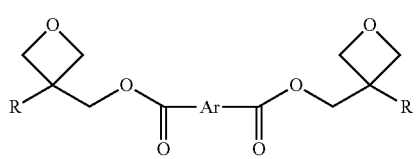
OX-A where for OX-A R generally is methyl or ethyl, and Ar generally is an aromatic ring or aromatic ring system. More specifically, when Ar is a phenyl ring with ortho substitution, R is methyl or ethyl; when Ar is a phenyl ring with meta substitution, R is methyl; when Ar is biphenyl with meta or para substitution, R may be methyl or ethyl; when Ar is the backbone of a bisphenol A, E, F or S, R may be methyl or ethyl; Ar is a polymeric structure with repeating units of an aromatic polyester (such as is shown in OX-12) or Ar is a phenyl ether, provided that Ar is not para substituted and with R being methyl or ethyl.

OX-B

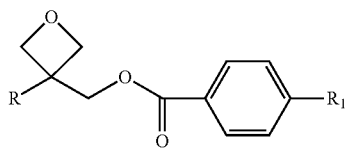

where for OX-B R generally is methyl or ethyl, and $R_1$ is an alkyl group of one to four carbon atoms, such as methyl, ethyl, propyls or butyls, particularly t-butyl.

Other oxetane-containing compounds that can be used in the inventive compositions include those oxetane resins commercially supplied by Nagase America Corporation, such as those available commercially under the ARON tradename including OXT-101, OXT-121, OXT-212, and OXT-221.

The epoxy-containing component and/or the oxetane-containing component should be used in an amount of about 1 to about 99 percent by weight of the total composition.

The cationic onium catalyst includes a cationic counter ion that may be within the following structure:

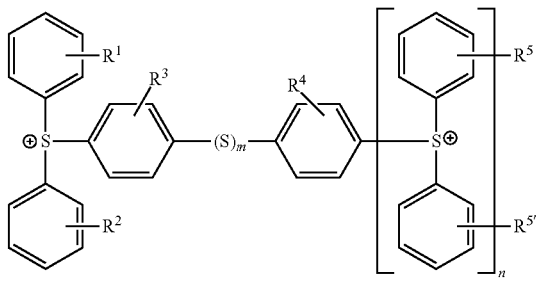

where $R^1$, $R^2$, $R^3$, $R^4$, $R^5$ and $R^{5'}$ may or may not be present, but when not present are hydrogen and when any are present may individually be selected from $C_{1-6}$ alkyl, $C_{2-6}$ alkenyl, halogen, hydroxyl and carboxyl, with $R^1$, $R^2$, $R^5$ and $R^{5'}$ being present individually up to 5 times on each aromatic ring to which it(they) is(are) attached, and $R^3$ and $R^4$ being present individually up to 4 times on each aromatic ring to which it(they) is(are) attached, n is 0-3 and m is 0-1.

The cationic onium catalyst includes a counter ion that may be selected from

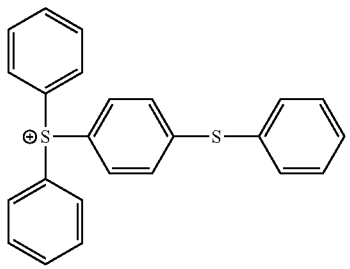

-continued

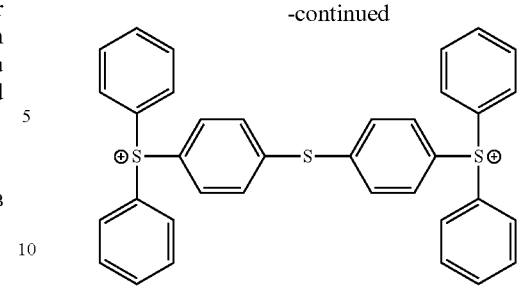

The cationic onium catalyst includes a counter ion that may be selected from

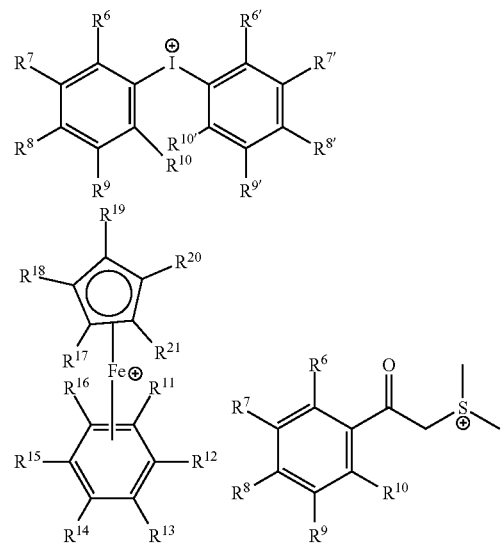

where for structure VI $R^6$, $R^7$, $R^8$, $R^9$ and $R^{10}$ may or may not be present, but when not present are hydrogen and when any are present may individually be selected from alkyl of from 1 to 5 carbon atoms, halogen, hydroxyl, and carboxyl; for structure VII $R^6$, $R^7$, $R^8$, $R^9$, $R^{10}$, $R^{6'}$, $R^{7'}$, $R^{8'}$, $R^{9'}$, and $R^{10'}$ may or may not be present, but when not present are hydrogen and when any are present may individually be selected from alkyl of from 1 to 5 carbon atoms, halogen, hydroxyl, and carboxyl; and for structure VIII $R^{11}$, $R^{12}$, $R^{13}$, $R^{14}$, $R^{15}$, $R^{16}$, $R^{17}$, $R^{18}$, $R^{19}$, $R^{20}$, and $R^{21}$ may or may not be present, but when not present are hydrogen and when any are present may individually be selected from alkyl of from 1 to 5 carbon atoms, halogen, hydroxyl, and carboxyl.

The cationic onium catalyst includes a counter ion that may be selected from

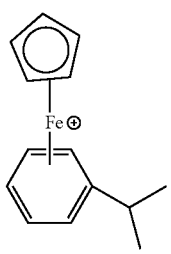

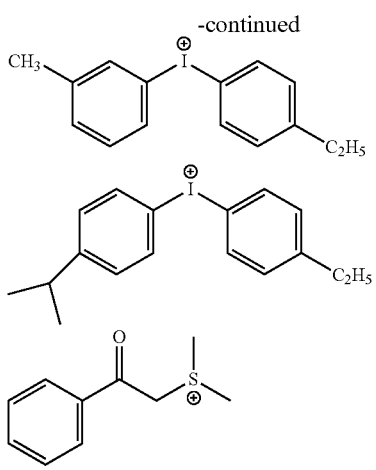

The cationic onium catalyst should be used in an amount within the range of about 0.1 to about 2 percent by weight of the total composition.

The transition metal salt includes a transition metal selected from copper, cobalt, vanadium, gold, silver, palladium, nickel, zirconium, iron, titanium, chromium, manganese, platinum, rhodium, iridium, ruthenium, osmium, hafnium, niobium, tantalum, molybdenum, tungsten, and rhenium.

The transition metal salt includes a salt selected from antimonates, phosphates, sulfonates, carboxylates, thiophenolates, ligand complexes thereof, some or all of which may be halogenated.

The transition metal salt should be used in an amount within the range of about 0.1 to about 10 percent by weight of the total composition A desirable ratio of the inventive adduct to cationic onium catalyst and transition metal salt is about 1:1:1 molar ratio. To tune the speed of cure and work life, this ratio can be changed to achieve desired curing and work life profile by one skilled in the art.

EXAMPLES

Both benzoin and furoin (shown below) are activated α-hydroxyketone compounds and act as efficient reducing agents for Cu(II) salts in a 3-component redox cationic system involving iodonium salts, as disclosed by Crivello.

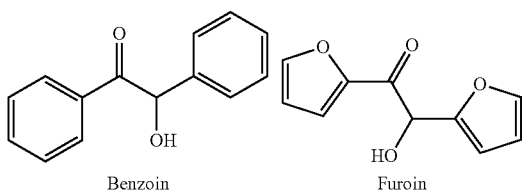

Benzoin    Furoin

However, the latency of these 3-component redox cationic systems is not sufficient to achieve good work life. For many low temperature cure applications, good viscosity stability of a few hours at room temperature is desired. Neither benzoin nor furoin themselves promote such latency.

Synthesis of Diels-Alder Adducts of Furoin

In this example, a latent reducing agent is formed through a Diels-Alder reaction product of furoin with compounds having either one or two maleimide functional groups. This adduct formation renders the α-hydroxyketone of furoin less activated and thus reduces the reactivity in a redox interaction with Cu(II) salts. While benzoin itself (like furoin itself) also acts a reducing agent, a Diels-Alder adduct cannot be formed with benzoin because of lack of diene unit in the structure (instead of furanyl rings, phenyl rings are present in benzoin).

Diels-Alder adducts were formed with furoin and two compounds having maleimide functional groups, as shown in the examples. The two maleimides are: SRM-1, a liquid bismaleimide resin of the structure shown below and made in accordance with U.S. Pat. No. 6,355,750 and N-cyclohexylmaleimide.

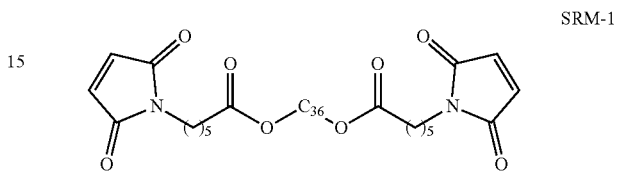

SRM-1

Synthesis of Adduct 1

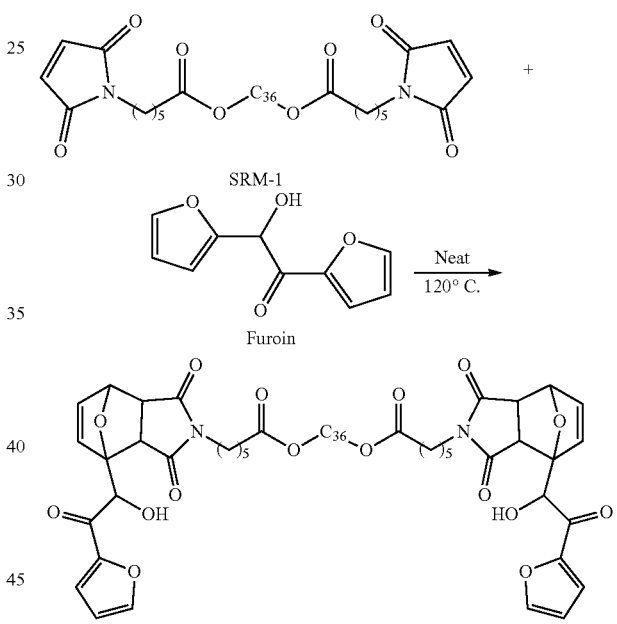

In a glass container equipped with a mechanical stirrer was taken a mixture of SRM-1 (57.3 g, 61 mmol), furoin (17.15 g, 89 mmol), and butyl hydroxy toluene ("BHT") (65 mg, 1000 ppm). The mixture was stirred at a temperature of 120° C. for a period of time of about 1 h, at which point a clear dark brown liquid was formed. The liquid was left at room temperature for two days. GPC performed on the liquid indicated the absence of any free furoin.

Synthesis of Adduct 2

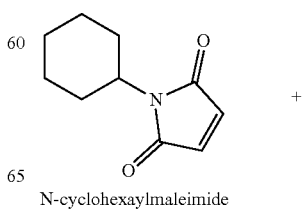

N-cyclohexaylmaleimide

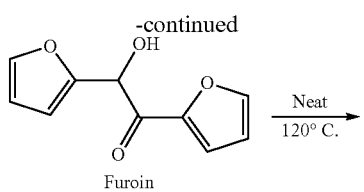

Furoin

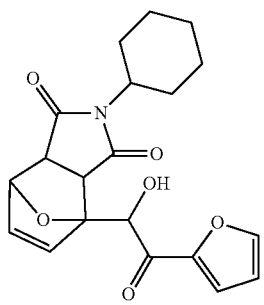

In a glass container equipped with a stirrer was taken a mixture of N-cyclohexylmaleimide (3.85 g, 21 mmoles), furoin (3.7 g, 19.3 mmoles) and BHT (8 mg, 1000 ppm). The mixture was stirred at a temperature of 120° C. for a period of time of about 1 hour, at which point a clear dark brown liquid was formed. The liquid was stored at room temperature for two days.

Formulation of Cationically Curable Compositions

Several compositions were prepared to evaluate low temperature cure capability coupled with work life viscosity stability. The identity and amount of the constituents used in the compositions are set forth in Table 1. Two control formulations (Formulations 1 and 5), with and without furoin, respectively, were also used for comparison of cure speed at low temperature and viscosity stability. Three formulations (Formulations 2-4) containing the latent reducing agent (Adduct 1) were used.

Each of the constituents was added with mixing in order to form the respective formulation. Each formulation was stored until ready for use.

TABLE 1

| Constituents | | Formulation/Amt (wt %) | | | | |
|---|---|---|---|---|---|---|
| Identity | Type | 1 | 2 | 3 | 4 | 5 |
| CELLOXIDE 2021P | Cycloaliphatic Epoxy | 21.00 | 21.00 | 21.00 | 21.00 | 21.10 |
| EPICLON 830S | Bisphenol-F Epoxy | 50.00 | 47.00 | 48.00 | 46.00 | 50.30 |
| NANOPOX E500 | Nanosilica in Bisphenol-F Epoxy | 26.00 | 25.60 | 25.60 | 25.70 | 26.10 |
| IRGACURE 250 | Iodonium salt | 1.42 | 1.37 | 1.38 | 1.35 | 1.45 |
| Furoin | Reducing agent | 0.56 | — | — | — | — |
| Adduct 1 | Latent reducing agent | — | 4.05 | 3.00 | 5.00 | — |
| Cu(II) 2-Ethylhexanoate | Copper salt | 1.03 | 0.99 | 1.00 | 0.98 | 1.05 |

Evaluation of Cure Temperatures by DSC

The onset and peak temperatures for Formulations 1-5 were studied using Differential Scanning calorimetry ("DSC"), according to ASTM D3418-15. Here, a DSC run scanned from an initial temperature of 20° C. up to 300° C. at a ramp rate of 5-10° C./min. The DSC data was collected and reported in Table 2.

The DSC data are collected and reported in Table 2.

The onset temperatures for Adduct 1-containing formulations (i.e., Formulation 2-4) appear to start at about 70° C. The Tgs for the Adduct 1-containing formulations were slightly lower than Formulation 1.

TABLE 2

| Physical | Formulation | | | | |
|---|---|---|---|---|---|
| Property | 1 | 2 | 3 | 4 | 5 |
| Onset T (° C.) | 57 | 78 | 79 | 78 | 96 |
| Peak T (° C.) | 69 | 88 | 87 | 90 | 107 |
| Delta H (J/g) | 287 | 254 | 245 | 199 | 232 |
| Tg (DSC, ° C.) | 35 | 22 | — | 20 | 24 |

Percent Cure

The percent cure for Formulations 1-5 was studied at different time intervals using isothermal DSC at a temperature of 100° C. The change in heat flow (W/g) was monitored over time as shown in Table 3. The method was setup to ramp to 100° C. in <1 minute after an initial 2 minute delay. The percent cure was calculated by dividing the heat flow observed at each time interval by the total heat and multiplying the result by 100.

TABLE 3

| Time | Formulation/Percent Cure | | | | |
|---|---|---|---|---|---|
| (mins) | 1 | 2 | 3 | 4 | 5 |
| 1 | 92.1 | 93.5 | 94.5 | 92.5 | 42.2 |
| 3 | 99.1 | 98.6 | 99.3 | 98.6 | 78.3 |
| 5 | 99.5 | 99.2 | 99.8 | 99.3 | 87.9 |
| 7 | 99.7 | 99.4 | 99.9 | 99.5 | 92.8 |
| 10 | 99.8 | 99.5 | 99.9 | 99.6 | 97.1 |

Importantly, while the onset for the free furoin-containing formulation (i.e., Formulation 1) was lower than the furoin adduct-containing formulations (i.e., Formulations 2-4) (see Table 2), the cure speeds for these formulations appeared to be similar as evidenced by similar level of percent cure observed (see Table 3). This shows the latency of inventive Formulations 2-4 without affecting their respective cure speeds. In contrast, Formulation 5, which contains no reducing agent but only the combination of transition metal salt/catalytic onium catalyst (i.e., Cu(II)-iodonium salt system), showed lower percent cure.

Worklife Evaluation

While similar percent cure was observed with furoin- and furoin adduct-containing formulations as shown above, the latency of Adduct 1-containing formulations (i.e., Formulations 2-4) was shown by a viscosity stability study, results of which are captured below in Table 4. Formulation 1 was determined to gel within 2.5 hours upon exposure (visual confirmation), while no significant viscosity change was observed in Formulations 2-4. While viscosity increase was observed for Formulations-2-4 in about 19 hours at room temperature, Formulations 2-4 were still in the liquid state even after 24 hours at room temperature. These results demonstrate significant improvement in viscosity stability of 3-component redox cationic system containing latent reducing agents while not affecting the cure speed.

23

TABLE 4

| Time | Formulation/Viscosity (cps) | | | | |
|---|---|---|---|---|---|
| (hours) | 1 | 2 | 3 | 4 | 5 |
| Initial | 2278 | 2485 | 2278 | 2693 | 2071 |
| 2.5 | Cured | 2071 | 1864 | 2278 | 2071 |
| 19 |  | 20919 | 28997 | 24233 | 2071 |
| 24 |  | 108000 | 94451 | 178000 | 2071 |

What is claimed is:

1. A reaction product of furoin or a furoin derivative and (a) a compound having one or more maleimide, nadimide or itaconimide functional groups and/or (b) a compound having one or more maleate or fumarate functional groups, wherein the compound having one or more maleate and fumarate functional groups is embraced by

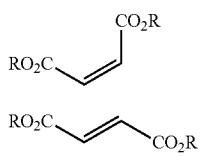

IV

V respectively, wherein each R is independently selected from alkyl groups having from 1 to about 20 carbon atoms, cycloalkyl groups having from 3 to about 10 carbon atoms, aryl groups and alkaryl groups having from 7 to about 10 carbon atoms.

2. The reaction product of claim 1, wherein the compound having one or more maleimide, nadimide, or itaconimide functional groups is embraced by

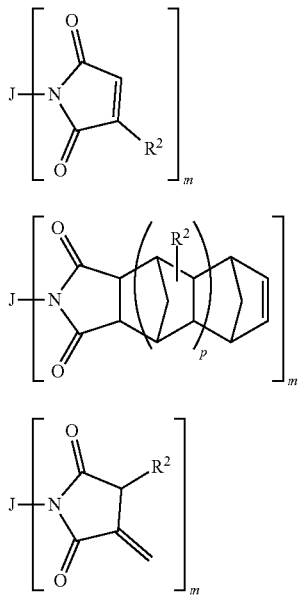

(I)

(II)

(III)

respectively, wherein:
m=1-15,
p=0-15,
each $R^2$ is independently selected from hydrogen or lower alkyl having from 1 to about 4 carbon atoms, and

24

J comprises a monovalent or a polyvalent moiety comprising organic or organosiloxane radicals, or a combinations thereof.

3. A curable composition comprising:
the reaction product of claim 1, and
an epoxy-containing or oxetane-containing component, a cationic onium catalyst and
a transition metal salt.

4. The curable composition of claim 3, wherein the epoxy-containing component is a member selected from the group consisting of cycloalphatic epoxy resins; $C_4$-$C_{28}$ alkyl glycidyl ethers; $C_1$-$C_{28}$ alkyl-glycidyl esters; $C_2$-$C_{28}$ alkenyl-glycidyl esters; $C_1$-$C_{28}$ alkyl-, mono- and poly-phenol glycidyl ethers; polyglycidyl ethers of pyrocatechol, resorcinol, hydroquinone, 4,4'-dihydroxydiphenyl methane (or bisphenol F), 4,4'-dihydroxy-3,3'-dimethyldiphenyl methane, 4,4'-dihydroxydiphenyl dimethyl methane (or bisphenol A), 4,4'-dihydroxydiphenyl methyl methane, 4,4'-dihydroxydiphenyl cyclohexane, 4,4'-dihydroxy-3,3'-dimethyldiphenyl propane, 4,4'-dihydroxydiphenyl sulfone, and tris(4-hydroxyphyenyl)methane; polyglycidyl ethers of the chlorination and bromination products of the above-mentioned diphenols; polyglycidyl ethers of novolacs; polyglycidyl ethers of diphenols obtained by esterifying ethers of diphenols obtained by esterifying salts of an aromatic hydrocarboxylic acid with a dihaloalkane or dihalogen dialkyl ether; polyglycidyl ethers of polyphenols obtained by condensing phenols and long-chain halogen paraffins containing at least two halogen atoms; phenol novolac epoxy resins; cresol novolac epoxy resins; and combinations thereof.

5. The curable composition of claim 3, wherein the oxetane-containing component is represented by:

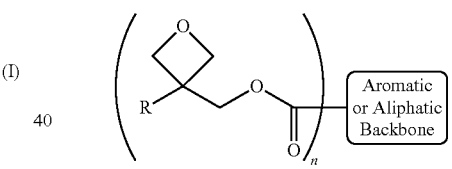

in which R is a methyl or ethyl group and n is 1 to 6.

6. The curable composition of claim 3, wherein the cationic onium catalyst includes a cationic counter ion within the following structure:

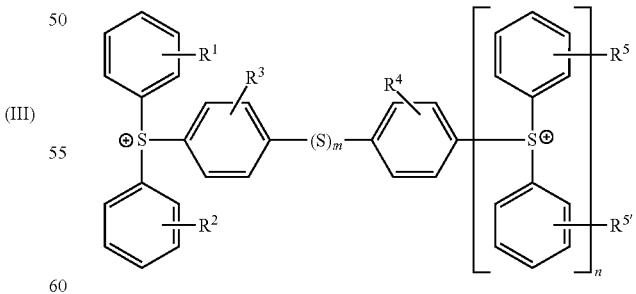

wherein $R^1$, $R^2$, $R^3$, $R^4$, $R^5$ and $R^{5'}$ may or may not be present, but when not present are hydrogen and when any are present may individually be selected from $C_{1-6}$ alkyl, $C_{2-6}$ alkenyl, halogen, hydroxyl and carboxyl, with $R^1$, $R^2$, $R^5$ and $R^{5'}$ being present individually up to 5 times on each aromatic ring to which it(they) is(are) attached, and $R^3$ and $R^4$ being present individually up to 4 times on each aromatic ring to which it(they) is(are) attached, n is 0-3 and m is 0-1.

7. The composition according to claim 3, wherein the cationic onium catalyst includes a counter ion selected from the group consisting of

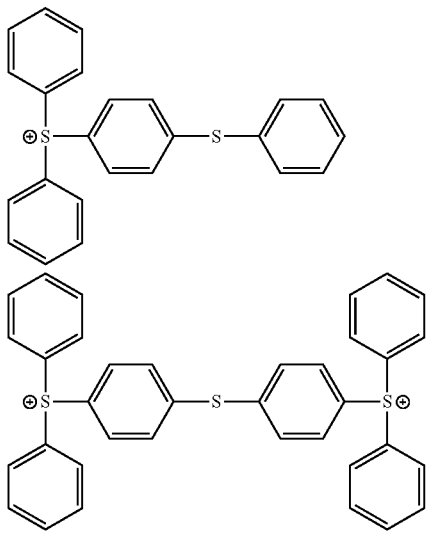

8. The composition according to claim 3, wherein the cationic onium catalyst includes a counter ion selected from the group consisting of

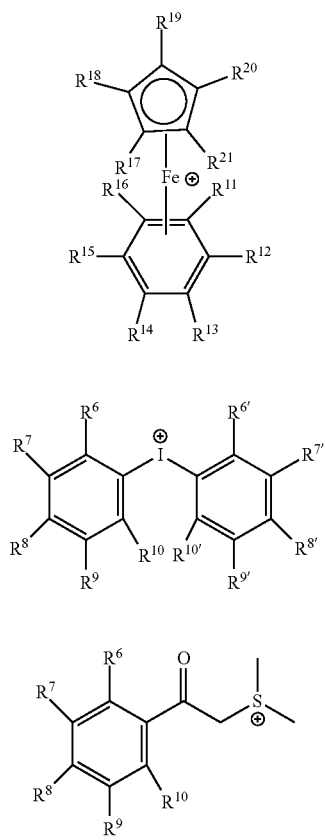

wherein for structure VI $R^{11}$, $R^{12}$, $R^{13}$, $R^{14}$, $R^{15}$, $R^{16}$, $R^{17}$, $R^{18}$, $R^{19}$, $R^{20}$, and $R^{21}$ may or may not be present, but when not present are hydrogen and when any are present may individually be selected from alkyl of from 1 to 5 carbon atoms, halogen, hydroxyl, and carboxyl; for structure VIII $R^6$, $R^7$, $R^8$, $R^9$ and $R^{10}$ may or may not be present, but when not present are hydrogen and when any are present may individually be selected from alkyl of from 1 to 5 carbon atoms, halogen, hydroxyl, and carboxyl, and for of structure VII $R^6$, $R^7$, $R^8$, $R^9$, $R^{10}$, $R^{6'}$, $R^{7'}$, $R^{8'}$, $R^{9'}$, and $R^{10'}$ may or may not be present, but when not present are hydrogen and when any are present may individually be selected from alkyl of from 1 to 5 carbon atoms, halogen, hydroxyl, and carboxyl.

9. The composition according to claim 3, wherein the cationic onium catalyst includes a counter ion selected from the group consisting of

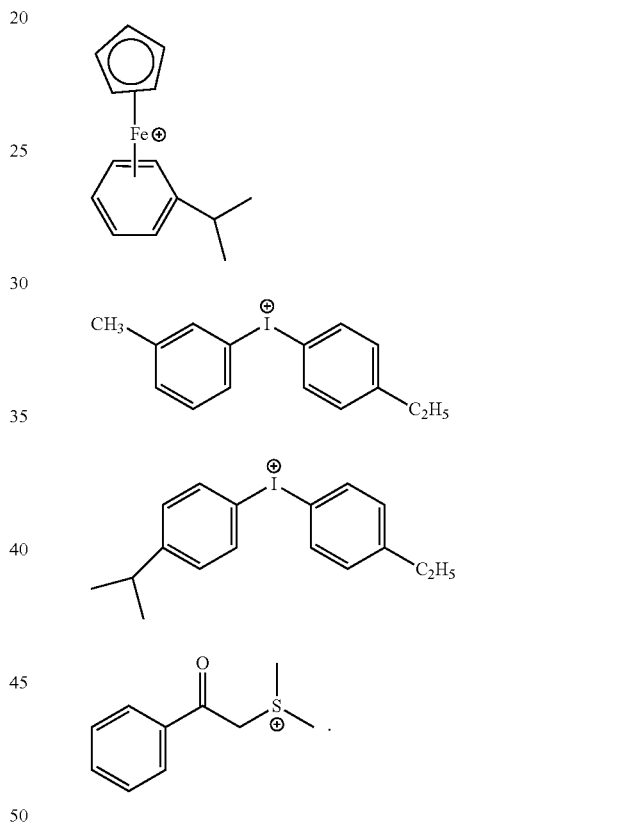

10. The composition according to claim 3, wherein the cationic onium catalyst is used in an amount within the range of about 0.1 to about 10 percent by weight of the total composition.

11. The composition of claim 3, wherein the transition metal salt includes a transition metal selected from the group consisting of copper, cobalt, vanadium, gold, silver, palladium, nickel, zirconium, iron, titanium, chromium, manganese, platinum, rhodium, iridium, ruthenium, osmium, hafnium, niobium, tantalum, molybdenum, tungsten, and rhenium.

12. The composition of claim 3, wherein the transition metal salt includes a salt selected from the group consisting of antimonates, phosphates, sulfonates, carboxylates, thiophenolates, ligand complexes thereof, some or all of which may be halogenated.

13. The reaction product of claim 3 selected from
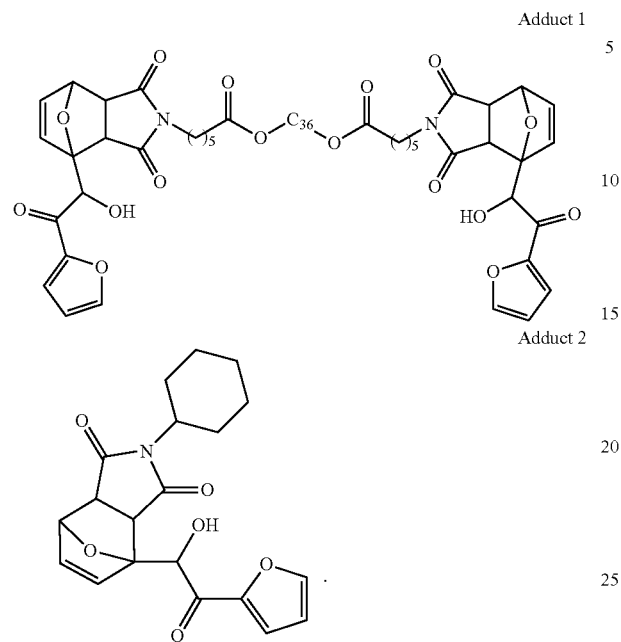
Adduct 1
Adduct 2
wherein $C_{36}$ is a linkage having 36 carbon atoms.
* * * * *